United States Patent [19]

Den Hartog et al.

[11] Patent Number: 5,091,393

[45] Date of Patent: Feb. 25, 1992

[54] TERTIARY 2,5-DIALKYL-3-PHENYLPIPERIDINE DERIVATIVES HAVING OPIATE-ANTAGONISTIC ACTIVITY

[75] Inventors: Jacobus A. Den Hartog; Ineke Van Wijngaarden; Martinus T. Tulp, all of Weesp, Netherlands

[73] Assignee: Duphar International Research B.V., Weesp, Netherlands

[21] Appl. No.: 528,895

[22] Filed: May 29, 1990

Related U.S. Application Data

[63] Continuation of Ser. No. 215,559, Jul. 6, 1988, abandoned.

[30] Foreign Application Priority Data

Jul. 9, 1987 [NL] Netherlands .................. 8701617

[51] Int. Cl.$^5$ .................. A61K 31/445; C07D 211/20
[52] U.S. Cl. .................... 514/317; 514/331; 546/237; 546/240; 546/192; 546/230; 546/233; 546/234; 546/235
[58] Field of Search ............. 546/230, 233, 234, 235, 546/192, 237, 240; 511/331, 317

[56] References Cited

U.S. PATENT DOCUMENTS

| | | | |
|---|---|---|---|
| 4,081,450 | 3/1978 | Zimmerman | 546/192 |
| 4,284,635 | 8/1981 | Zimmerman | 546/192 |
| 4,593,037 | 6/1986 | Sarges | 514/317 |

OTHER PUBLICATIONS

*Chemical Abstracts*, 74:22700h (1971), "Butyrophenone Derivatives."

M. Iorio et al., *J. Med. Chem.*, 21(8), "Nalorphine-like properties of some 2,3-dimethyl-3-arylpiperdines (1978)".

Primary Examiner—Richard L. Raymond
Assistant Examiner—Mark W. Russell
Attorney, Agent, or Firm—Stevens, Davis, Miller & Mosher

[57] ABSTRACT

The invention relates to a group of tertiary 2,5-dialkyl-3-phenylpiperidine derivatives, having opiate-antagonistic activity represented by general formula 4,

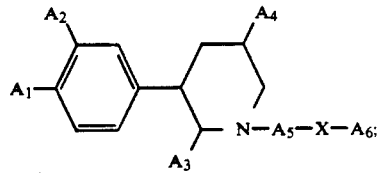

wherein
$A_1$ is hydrogen, an optionally esterified hydroxyl group or mercapto group, a group $NHA_8$ or $-CONHA_8$, wherein $A_8$ is hydrogen, alkyl having 1-6 C-atoms or alkylcarbonyl having 2-7 C-atoms;

$A_2$ is hydrogen or, when $A_1$ is hydrogen, one of the other meanings of $A_1$, or $A_1$ and $A_2$ together with the 2 carbon atoms of the benzene ring, constitute a heterocyclic group which consists of five or six ring atoms and which comprises a group $-NH-$ and optionally as a second hetero atom may comprise an oxygen atom, sulphur atom or nitrogen atom;

$A_3$ and $A_4$ independently of each other are straight or branched alkyl or alkenyl having 1-6 C-atoms;

$A_5$ is a straight or branched alkylene chain having 2-8 C-atoms;

X is the carbonyl group or ketalized carbonyl group or the group $>CHOH$, $-CONH-$, $-NHCO-$, methylene, $>CHC_6H_5$, or an oxygen atom or sulphur atom;

$A_6$ is an alkyl group, cycloalkyl group or cycloalkylalkyl group having at most 10 C-atoms and optionally substituted with one or more groups $A_7$, or is a phenyl group or phenylalkyl group having 1-4 C-atoms in the alkyl group and optionally substituted with one or more groups $A_7$, and $A_7$ is alkyl, alkoxy or alkylthio having 1-4 C-atoms, amino, mono- or dialkylamino having 1-4 C-atoms per alkyl group, hydroxyalkyl, alkylcarbonyl, alkylaminocarbonyl or alkoxycarbonyl having 1-4 C-atoms in the alkyl group, nitro, cyano, halogen, trifluoromethyl, trifluoromethoxy, alkylsulphonyl having 1-4 C-atoms, or aminosulphonyl.

These compounds have a pure opiate-antagonistic activity, i.e. without an agonistic activity component.

4 Claims, No Drawings

TERTIARY 2,5-DIALKYL-3-PHENYLPIPERIDINE DERIVATIVES HAVING OPIATE-ANTAGONISTIC ACTIVITY

This application is a continuation of application Ser. No. 215,559, filed July 6, 1988 now abandoned.

The invention relates to tertiary 2,5-dialkyl-3-phenyl-piperidine derivatives having opiate-antagonistic properties. The invention also relates to the salts and pro-drugs of the said compounds, to a method of preparing the active compounds, and to pharmaceutical compositions comprising at least one of these new compounds or a salt or prodrug thereof as the active substance.

It is known that in animals and man receptors are present with which endogenous opioids, i.e. opioids which naturally occur in the body, for example, the enkephalines, interact. Although the activity of these endogenous opioids may be very favourable in a number of cases, a large number of conditions are also known in which the effects of these endogenous opioids are just particularly negative. Compounds which show an antagonistic activity against these endogenous opioids may hence be used in the treatment of a number of syndromes in man. Such opiate-antagonists may also be used to counteract the effects of exogenous opiates, for example, morphine. For these purposes substances are preferably used which have a pure opiate-antagonistic effect without an agonistic component, so as to avoid the danger of undesired addictive properties associated with opiate-agonism.

Known compounds having a pure opiate-antagonistic activity are naloxone (formula 1a), naltrexone (formula 1b) and nalmephene (formula 1c). These compounds which structurally are closely related to each other, are derived from the known exogenous opiate-agonist morphine.

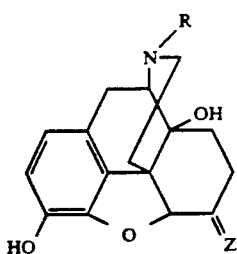

(1)

Furthermore, a few compounds having opiate-antagonistic activity are known which are derived from the 4-phenylpiperidine opiate agonistic derivative meperidine which has a much simpler structure (Nature, 275, (1978), p. 332); the activity of these compounds is approximately equal to that of naloxone.

Finally, an opiate-antagonistic activity, albeit in general moderate (up to at most 25% of naloxone) has also been described for a few compounds from the corresponding 3-phenylpiperidine series. It concerns alkylated 3-phenylpiperidines of formula 2 which are known from British Patent Application 2,152,499

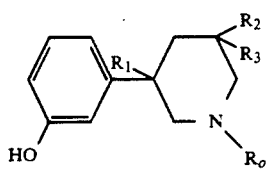

(2)

wherein $R_0$ may be hydrogen, alkyl, alkenyl, alkynyl, aralkyl, 2-tetrahydrofurylmethyl or cycloalkylmethyl, $R_1$ and $R_2$ are inter alia alkyl, and $R_3$ is hydrogen or alkyl; and compounds of formula 3 which are known from J. Pharm. Pharm. 35, (1983), p. 765:

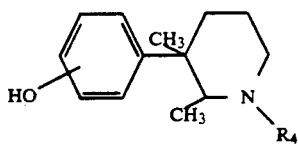

(3)

wherein $R_4$ may inter alia be allyl, cyclopropylmethyl or alkyl.

It has been found that the new 2,5-dialkyl-3-phenyl piperidine derivatives of the general formula 4

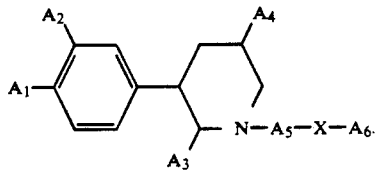

and the salts thereof have a surprisingly strong pure opiate-antagonistic activity.

In formula 4 the symbols have the following meanings:

$A_1$ is hydrogen, an optionally esterified hydroxyl group or mercapto group, a group —$NH_8$ or —$CONHA_8$, wherein $A_8$ is hydrogen, alkyl having 1–6 C-atoms or alkylcarbonyl having 2–7 C-atoms;

$A_2$ is hydrogen or, when $A_1$ is hydrogen, one of the other meanings of $A_1$, or $A_1$ and $A_2$ together with the 2 carbon atoms of the benzene ring, constitute a heterocyclic group which consists of five or six ring atoms and which comprises a group —NH— and optionally as a second hetero atom may comprise an oxygen atom, sulphur atom or nitrogen atom;

$A_3$ and $A_4$ independently of each other are straight or branched alkyl or alkenyl having 1–6 C-atoms;

$A_5$ is a straight or branched alkylene chain having 2–8 C-atoms;

X is the carbonyl group or ketalised carbonyl group or the group >CHOH, —CONH—, —NHCO—, methylene, >CHC$_6$H$_5$, or an oxygen atom or sulphur atom;

$A_6$ is an alkyl group, cycloalkyl group or cycloalkylalkyl group having at most 10 C-atoms and optionally substituted with one or more groups $A_7$, or is a phenyl group or phenylalkyl group having 1–4 C-atoms in the alkyl group and substituted with one or more groups $A_7$, and $A_7$ is alkyl, alkoxy or alkylthio having 1–4 C-atoms, amino, mono- or dialkylamino having 1–4 C-atoms per alkyl group, hydroxyalkyl, alkylcarbonyl, alkylaminocarbonyl or alkoxycarbonyl having 1–4 C-atoms in the alkyl group, nitro, cyano, halogen, trifluoromethyl, trifluoromethoxy, alkylsulphonyl having 1–4 C-atoms, or aminosulphonyl.

The compounds which are to be preferred on the basis of their properties are compounds of formula 4, wherein the symbols have the following meanings, and the salts and prodrugs thereof:

$A_1$ hydrogen, hydroxyl or esterified hydroxyl, or aminocarbonyl;
$A_2$ hydrogen or, when $A_1$ is hydrogen, hydroxyl, esterified hydroxyl or aminocarbonyl;
$A_3$ alkyl having 1–3 C-atoms;
$A_4$ alkyl having 1–3 C-atoms;
$A_5$ a straight alkylene chain having 2–4 C-atoms;
X carbonyl or the group >CHOH;
$A_6$ cyclohexyl or phenyl.

Compounds according to the invention which are to be preferred in particular are the compounds of formula 4 wherein the symbols have the following meanings:

| | $A_1$ | $A_2$ | $A_3$ | $A_4$ | $A_5$ | X | $A_6$ |
|---|---|---|---|---|---|---|---|
| 1. | OH | H | $CH_3$ | $CH_3$ | $(CH_2)_3$ | C=O | cyclohexyl |
| 2. | $OCOCH_3$ | H | $CH_3$ | $CH_3$ | $(CH_2)_3$ | C=O | cyclohexyl |
| 3. | $OCOC_6H_5$ | H | $CH_3$ | $CH_3$ | $(CH_2)_3$ | C=O | cyclohexyl |
| 4. | H | OH | $CH_3$ | $CH_3$ | $(CH_2)_3$ | C=O | cyclohexyl |
| 5. | OH | H | $n.C_3H_7$ | $CH_3$ | $(CH_2)_3$ | C=O | cyclohexyl |
| 6. | OH | H | $CH_3$ | $C_2H_5$ | $(CH_2)_3$ | C=O | cyclohexyl |
| 7. | OH | H | $CH_3$ | $CH_3$ | $(CH_2)_4$ | C=O | cyclohexyl |
| 8. | OH | H | $CH_3$ | $CH_3$ | $(CH_2)_3$ | CHOH | cyclohexyl |
| 9. | OH | H | $CH_3$ | $CH_3$ | $(CH_2)_3$ | C=O | phenyl |
| 10. | OH | H | $CH_3$ | $CH_3$ | $(CH_2)_3$ | CHOH | phenyl |

The compounds of formula 4 comprise at least three chiral centres, namely the carbon atoms 2, 3 and 5 of the piperidine ring to which the alkyl substituent $A_3$, the phenyl group and the alkyl substituent $A_4$, respectively, are bound. The invention relates to the various isomers of the compounds of formula 4 and to racemates and mixtures of diastereomers.

Suitable acids with which the compounds according to the invention can form pharmaceutically acceptable acid addition salts are, for example, hydrochloric acid, sulphuric acid, phosphoric acid, nitric acid, and organic acids, for example, citric acid, fumaric acid, maleic acid, tartaric acid, acetic acid, benzoic acid, p-toluene sulphonic acid, methane sulphonic acid, naphthalene sulphonic acid, and the like.

Prodrugs are to be understood to be derivatives of the compounds of formula 4 which as such are inactive and which, after administration into the body, are converted into an active substance of formula 4.

On the basis of their opiate-antagonistic activity, compounds according to the invention are extremely suitable for the treatment of those diseases and conditions in man, in which endogenous opioids play a part. Examples are: schizophrenia, depression, epilepsy and other diseases assocated with the central nervous system, shock, stroke and other disorders associated with the heart and vascular system, ulcers, obesity, respiratory disorders and several types of tumours, especially neuroblastoma. They may also be used for the treatment of patients after an overdose of exogenous opiates, to stop anaesthesia with exogenous opiates and as an auxiliary agent to prevent recidivism in former addicts of exogenous opiates. The compounds according to the invention have been examined for the activities below in a number of relevant test models. Naloxon was used as the reference substance.

1. OPIATE-(ANT)AGONISTIC ACTIVITY IN VITRO

1. Affinity to Opiate Receptors

The affinity to (mainly /μ-type) opiate receptors was determined by studying the displacement of [$^3$H]-naloxon in homogenates of rat brains (Pert and Snyder, Molecular Pharmacology 10, 868–879 (1974)). The results were expressed in $K_i$-values.

1.2 Opiate-(Ant)Agonistic Activity on the Isolated Guinea Pig Ileum and Mouse Vas Deferens.

The opiate-antagonistic activity was determined by studying the antagonism of the effect of the agonists morphine and ethylketazocine on the electrically stimulated guinea pig ileum (/μ-type and (mainly) k-type of opiate-antagonism, respectively) and the antagonism of the effect of the agonist leucine- enkephaline on the electrically stimulated mouse vas deferens (δ-type of opiate-antagonism). The results were expressed in $pA_2$ values.

In order to establish any opiate-agonistic activity, the effect of the test compounds on the electrically stimulated guinea pig ileum and mouse vas deferens was determined. In order to find out whether any found effect was caused by opiate-agonism, the reversal of this possible effect by the antagonist naloxon was studied. The above experiments were carried out as described in Magnan et al, Naunyn Schmiedeberg's Arch. Pharmacol. 319, 197–205 (1982), or, for the experiments with ethylketazocine, completely analogously to the experiments with morphine described in the said paper.

2. OPIATE-(ANT)AGONISTIC ACTIVITY IN VIVO

Opiate-antagonistic activity in vivo was determined by studying the antagonism of morphine-induced analgesia in mice, measured according to Bianchi and Francheschini, Br. J. Pharmacol. Chemother. 9, 280–284 (1954). The test compounds were administered subcutaneously (sc) or orally (po) in a series of dosages, using five animals for each dose, and the results were expressed in $ED_{50}$ values. In order to establish any opiate-agonistic activity it was determined whether the highest dose used in the antagonistic test had any analgetic activity.

The new compounds according to the invention and the salts and prodrugs thereof may be prepared in manner known for the synthesis of analogous compounds.

The invention therefore also relates to a method of preparing new tertiary 2,5-dialkyl-3-phenyl piperidine derivatives of formula 4, wherein the symbols have the meanings mentioned hereinbefore, and the salts and prodrugs thereof.

Suitable methods of preparing the compounds of formula 4 comprise as a rule the reaction of a secondary amine of formula 5:

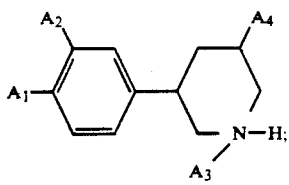

wherein $A_1$-$A_4$ have the above-mentioned meanings, with a compound of the general formula 6:

$$L-A_5-X'-A_6 \qquad (6)$$

wherein $A_5$ and $A_6$ have the above-mentioned meanings, L is a halogen atom or a tosyloxy group and $X'$ is a carbonyl group, 1,3-dioxolane group, methylene group, or $CHC_6H_5$-group, or an oxygen atom or sulphur atom.

The reaction is preferably carried out in an inert solvent, for example, dimethyl formamide or acetonitrile, or without a solvent, at a temperature of 0°-180° C., preferably 20°-80° C., for 1-48 hours; a base, for example, triethyl amine or sodium carbonate, may be added to the reaction mixture, or an excess of the amine (5) may be used; furthermore, in case L is a chlorine atom, NaI may be added to the reaction mixture as a catalyst.

By treating with a dilute acid, for example, hydrochloric acid, the resulting compounds of formula 4, wherein X is a 1,3-dioxolane group, may be converted, if so desired, into the analogous compounds wherein X is the carbonyl group.

The resulting compounds of formula 4, wherein X is the carbonyl group, may then be further converted into analogous compounds, wherein X is a >CHOH group, by treatment with a reducing agent, for example, $NaCNBH_4$, in a manner known per se (J. Am. Chem. Soc. 93, 2897 (1971)).

Compounds of the general formula 4, wherein X is the group —CONH— or —NHCO—, can be obtained in a manner known per se (see Patai, "The Chemistry of the amino group", Interscience Publishers, New York, 1968 and Zabicky, "The chemistry of amides", Interscience Publishers, New York, 1956), also starting from an amine of formula 5.

The compounds of formula 5, wherein $A_1$-$A_4$ have the above-mentioned meanings, used as starting substances can inter alia, be obtained in the following manner. Reaction of a ketone of formula 7

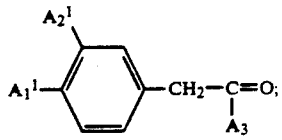

wherein $A_1'$ and $A_2'$ have the meanings mentioned for $A_1$ and $A_2$, with the proviso that reactive hydrogen atoms present therein have been replaced by a protective group, while $S_3$ has the above-mentioned meaning, with an acrylamide derivative of formula 8:

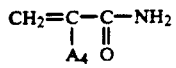

wherein $S_4$ has the above-mentioned meaning, results, in a manner known for analogous compounds (Synthesis, 305, 1985), in the ring system of formula 9:

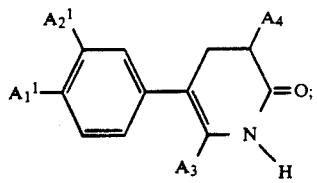

The desired amine of formula 5 can be obtained from compounds of formula 9 by two successive reducing steps, in which either first the double bond and then the keto group, or first the keto group and then the double bond, is converted, optionally succeeded by removal of protective groups.

The reduction of the keto group is carried out in a manner known per se by reaction with a metal hydride, for example, lithium aluminium hydride (Gaylord, "Reduction with complex metal hydrides", Interscience Publishers, New York, 1956). The reduction of the double bond is also carried out in a manner known per se by catalytic hydrogenation with, for example, platinum oxide as a catalyst (Rylander, "Catalytic hydrogenation over platinum metals", Academic Press, New York, 1967).

The ketones of formula 7 are partly known compounds and in so far as they are new compounds, they can be prepared in a manner known for the preparation of analogous ketones. The acrylamide derivatives of formula 8 are known compounds.

The invention will now be described in greater detail with reference to the ensuing specific examples. The compounds were obtained as a high-melting-point oil the boiling point of which could not be determined as a result of decomposition. The compounds were characterized by means of $^1H$ or $^{13}C$ NMR.

EXAMPLE 1-(4-cyclohexyl-4-oxobutyl)-2,5-dimethyl-3-(4-hydroxyphenyl)piperidine 1) The preparation of the compound 2,5-dimethyl-3-(4-methoxyphenyl)piperidine was carried out in two manners:

Method A: 1 g of platinum chloride was added to a solution of 15 g (65 mmol) of 3,6-dimethyl-5-(4-methoxyphenyl)-3,4-dihydro-2-pyridone (Synthesis 305, 1985) in 75 ml of glacial acetic acid and the mixture was hydrogenated at room temperature and a pressure of 52 psi for 8 hours. The catalyst was then removed by filtration and the glacial acetic acid was evaporated under reduced pressure. The residue was dissolved in ethyl acetate and washed successively with ammonia (5%), water and a saline solution. The organic layer was dried on sodium sulphate, filtered and evaporated under reduced pressure. The resulting crude product (15 g) was purified chromatographically over a dry column of 700 g of silcagel (Merck, grain size 0.063-0.200 mm) using a mixture of dichloromethane and acetone (95:5) as an eluent. After evaporating the correct fractions, 5.8 g (38%) of the desired 3,6-dimethyl-5-(4-methoxyphenyl)-3,4,5,6-tetrahydro-2-pyridone were obtained in addition to 3.5 g (23%) of the starting compound.

A solution of 5.8 g (25 mmol) of 3,6-dimethyl-5-(4-methoxyphenyl)-3,4,5,6-tetrahydro-2-pyridone in 60 ml of dry tetrahydrofuran was added dropwise under nitrogen to a suspension of 1.63 g of lithium aluminium hydride (63 mmol) in 25 ml of dry tetrahydrofuran. After the reaction mixture had been refluxed for 2 hours, it was cooled and, while cooling with ice, 1.6 ml of water in 10 ml of tetrahydrofuran, 3.2 ml of 2N sodium hydroxide and 3.2 ml of water were successively added dropwise. After refluxing for a short period of time the resulting precipitate was filtered off and rinsed thoroughly with warm tetrahydrofuran; the filtrate was evaporated under reduced pressure. The resulting crude product was purified by means of flash chromatography over 100 g of silicagel (Merck, grain size 0.040–0.063 mm) using a mixture of ethyl acetate, methanol and concentrated ammonia (93:6.5:0.5) as an eluent. After combining and evaporating the desired fractions, totally 3.6 g (65%) of 2,5-dimethyl-3-(4-methoxyphenyl)piperidine were obtained.

Method B: A solution of 6.95 g (30 mmol) of 3,6-dimethyl-5-(4-methoxyphenyl)-3,4-dihydro-2-pyridone in 70 ml of tetrahydrofuran was added dropwise under nitrogen to a suspension of 1.7 g (45 mmol) of lithium aluminium hydride in 50 ml of dry tetrahydrofuran. After the reaction mixture had been refluxed for 90 minutes, it was cooled and 1.7 ml of water in 10 ml of tetrahydrofuran, 3.4 ml of 2N sodium hydroxide and 3.4 ml of water were added dropwise successive while cooling with ice. After refluxing for a short period of time the resulting precipitate was filtered off and rinsed thoroughly with warm tetrahydrofuran; the filtrate was evaporated under reduced pressure. The resulting crude product (6.5 g) was dissolved, without further purification, in 75 ml of absolute ethanol. 0.5 g of platinum oxide were added to this solution and the mixture was hydrogenated at room temperature and atmospheric pressure for 30 minutes. After removing the catalyst by filtration the ethanol was evaporated under reduced pressure. The resulting crude product (6 g) was purified by means of flash chromatography over 100 g of silicagel (Merck, grain size 0.040–0.063 mm) using a mixture of ethyl acetate, methanol and concentrated ammonia (93:6.5:0.5) as an eluent, succeeded by flash chromatography over 100 g of silicagel (Merck, grain size 0.040–0.063 mm) using a mixture of dichloromethane, methanol and concentrated ammonia (93:6.5:0.5) as an eluent. After combining and evaporating the desired fractions, totally 2.5 g (38%) of 2,5-dimethyl-3-(4-methoxyphenyl)piperidine were obtained.

2) A solution of 2.2 g (10 mmol) of 2,5-dimethyl-3-(4-methoxyphenyl)piperidine in 15 ml of a 45% solution of hydrogen bromide in acetic acid was heated at 95° C. for 1 hour. After the addition of another 5 ml of the 45% solution of hydrogen bromide in acetic acid the mixture was heated at 95° C. for a further 90 minutes. After cooling, the reaction mixture was poured on ice, rendered basic with concentrated ammonia and extracted twice with dichloromethane. The organic layer was dried on sodium sulphate, filtered and evaporated under reduced pressure. In this manner 1.7 g (83%) of substantially pure 2,5-dimethyl-3-(4-hydroxyphenyl)-piperidine were obtained.

3) 0.96 g (9 mmol) of sodium carbonate, 1.35 g (9 mmol) of sodium iodide and 2.1 g (9 mmol) of 2-(3-chloropropyl)-2-cyclohexyl-1,3-dioxolane were added to a solution of 1.7 g (8.3 mmol) of 2,5-dimethyl-3-(4-hydroxyphenyl)piperidine in 10 ml of dimethylformamide and the resulting reaction mixture was stirred at a temperature of 80° C. for 16 hours. After cooling, the reaction mixture was poured on ice and extracted three times with ethyl acetate. After evaporating the organic layer under reduced pressure, the residue was dissolved in a mixture of 20 ml of dimethylformamide and 40 ml of 2N hydrochloric acid and stirred for 1 hour so as to split the dioxolane group present. The solution was then extracted three times with diethyl ether, rendered basic by the addition of concentrated ammonia and extracted three times with ethyl acetate. The resulting organic layer was washed three times with water and once with a concentrated saline solution, dried on sodium sulphate an evaporated under reduced pressure. The resulting crude product (2.3 g) was purified by means of flash chromatography over 75 g of silicagel (Merck, grain size 0.040–0.063 mm) using a mixture of dichloromethane, methanol and concentrated ammonia (95:4.5:0.5) as an eluent. After combining and evaporating the desired fractions, totally 1.2 g (46%) of 1-(4-cyclohexyl-4-oxobutyl)-2,5-dimethyl-3-(4-hydroxyphenyl)piperidine were obtained (compound no. 1).

The above-mentioned compounds no. 4, 5, 6, 7 and 9 were obtained in an analogous manner. The remaining compounds were prepared in a manner known per se starting from compound no. 1 (2, 3 and 8) and no. 9 (10), respectively.

We claim:

1. Compounds of formula 4

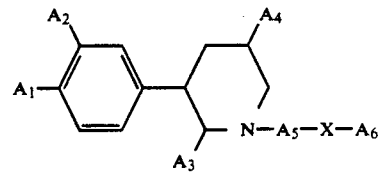

and salts thereof, wherein
$A_1$ is an optionally esterified hydroxyl group wherein the esterifying group is acetate or benzoate;
$A_2$ is hydrogen;
$A_3$ and $A_4$ independently of each other are straight or branched alkyl or alkenyl having 1–6 C-atoms;
$A_5$ is alkylene having 3–5 C-atoms;
X is carbonyl or the group —CH(OH)—; and
$A_6$ is cyclohexyl or phenyl.

2. Compounds of formula 4

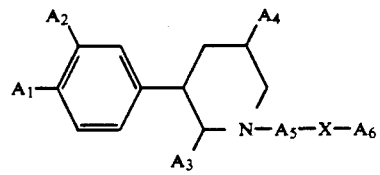

and salts thereof, wherein
$A_1$ is hydroxyl or esterified hydroxy wherein the esterifying group is acetate or benzoate;
$A_2$ is hydrogen;
$A_3$ is alkyl having 1–3 C-atoms;
$A_4$ is alkyl having 1–3 C-atoms;
$A_5$ is a straight alkylene chain having 2–4 C-atoms;
X is carbonyl or the group CHOH; and
$A_6$ is cyclohexyl or phenyl.

3. Pharmaceutical compositions having opiate-antagonistic activity which comprise an opiate-antagonistically effective amount of at least one compound as claimed in claim 1 as the active substance and a pharmaceutically acceptable carrier.

4. Pharmaceutical compositions having opiate-antagonistic activity which comprise an opiate-antagonistically effective amount of at least one compound as claimed in claim 2 as the active substance, and a pharmaceutically acceptable carrier.

* * * * *